United States Patent [19]

Bliem et al.

[11] Patent Number: 4,960,706
[45] Date of Patent: Oct. 2, 1990

[54] STATIC OXYGENATOR FOR SUSPENSION CULTURE OF ANIMAL CELLS

[75] Inventors: Rudolf F. Bliem, Castro Valley; James F. Long, San Francisco, both of Calif.

[73] Assignee: Baxter International, Inc., Deerfield, Ill.

[21] Appl. No.: 328,629

[22] Filed: Mar. 27, 1989

[51] Int. Cl.⁵ ............................ C12M 3/00; C10J 1/08
[52] U.S. Cl. ..................... 435/284; 435/313; 435/314; 435/315; 435/818; 261/122
[58] Field of Search ............... 435/284, 286, 287, 311, 435/313–315, 812, 818; 422/45; 261/87, 94, 100, 122, 123, 126

[56] References Cited

U.S. PATENT DOCUMENTS

| 4,087,327 | 5/1978 | Feder et al. | 435/285 X |
| 4,264,739 | 4/1981 | Grabner et al. | 435/313 X |
| 4,535,062 | 8/1985 | Müller | 435/311 X |
| 4,545,945 | 10/1985 | Präve et al. | 261/123 X |
| 4,643,972 | 2/1987 | Young | 435/252 |
| 4,649,117 | 3/1987 | Famillette | 435/313 |
| 4,668,632 | 5/1987 | Young et al. | 435/284 |
| 4,725,548 | 2/1988 | Karrer | 435/240.1 |
| 4,727,040 | 2/1988 | Freedman et al. | 435/315 |
| 4,749,654 | 6/1988 | Karrer et al. | 435/240.25 |

FOREIGN PATENT DOCUMENTS

WO8607605 12/1986 PCT Int'l Appl. .
WO8702054 4/1987 PCT Int'l Appl. .
1308623 7/1985 U.S.S.R. .

OTHER PUBLICATIONS

Glacket, M. W., et al., "Mammalian Cell Culture: Engineering Principles and Scale-Up", (1983).
Whiteside, J. P., et al., "The Use of Caged Aeration for The Growth of Animal Cells on Microcarriers", Develop. Biol. Standard., vol. 60, pp. 283–290, (1985).
Rebsamen, E., et al., "Use of a Dynamic Filtration Method for Separation of Animal Cells", Devlop. Biol. Standard., vol. 66, pp. 273–277, (1987).
Karinger, H., "Animal Cell Culture: Biological and Technological Aspects", Proc. 4th European Congress on Biotechnology, 1987, vol. 4.

Primary Examiner—Robert J. Warden
Assistant Examiner—Rebekah A. Griffith
Attorney, Agent, or Firm—St. Onge Steward Johnston & Reens

[57] ABSTRACT

A static oxygenator for oxygenating a liquid, particularly a suspension culture of animal cells in a liquid culture medium, comprised of a bottom gassing portion comprised of generally concentric vertically oriented hollow cylinders of porous gas-permeable, liquid-impermeable material, and an upper degassing section comprised of vertical extensions of the concentric cylinders such that at least one liquid overflow weir is provided at the juncture between the bottom and upper sections. Gas directed into the bottom of the annular space between the concentric cylinders rises therein and, across the porous material, oxygenates liquid in contact therewith or in proximity thereto up to the point where the liquid overflows the weir, and the gas then continues up the annular space in the vertical extensions for degassing through the porous material above the liquid level.

12 Claims, 2 Drawing Sheets

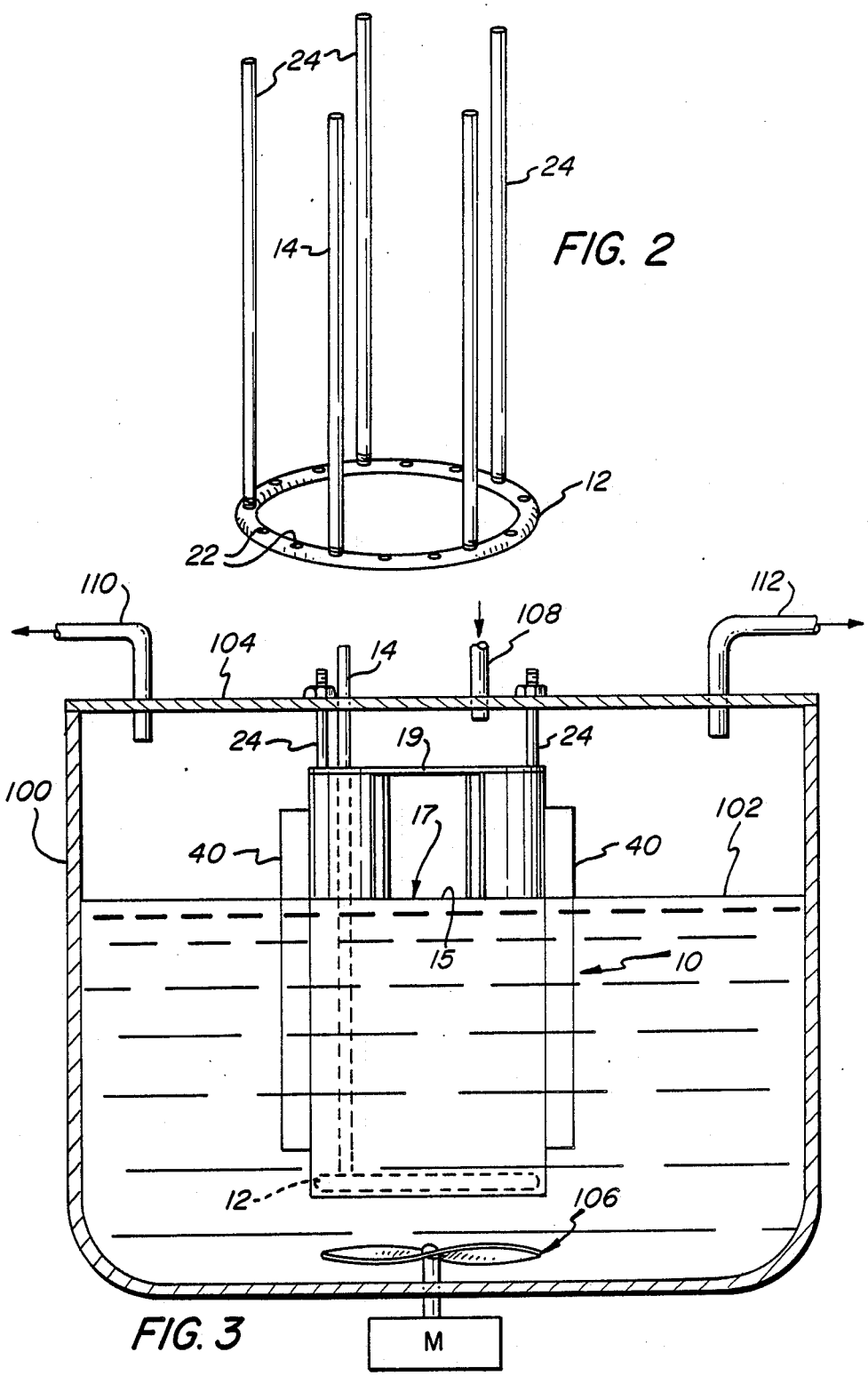

STATIC OXYGENATOR FOR SUSPENSION CULTURE OF ANIMAL CELLS

BACKGROUND OF THE INVENTION

The present invention relates to the in vitro culture of animal cells and, more particularly, to an apparatus for providing oxygen to animal cells which are in suspension culture with culture medium in a suspension culture vessel.

The in vitro culture of animal cells, particularly for purposes of recovering proteins either normally secreted by such cells or secreted by such cells by virtue of manipulation of their genetic machinery, has assumed increasingly greater prominence as a consequence of the increasing need for large quantities of proteins for therapeutic, diagnostic and investigative purposes, and the recognition that animal cells (per se. or as a hybrid partner, or as a host for an exogeneous gene) offer the best source of proteins which are the same as or closely similar o those actually employed by animals (e.g., humans) in vivo in carrying out regulatory, immune response, and other like functions.

Despite the recognized advantages of, and needs for, in vitro animal cell culture, the culture of cells outside the animal body is a difficult proposition at best, made even more difficult by the present-day demand that such processes be carried out efficiently and economically so as to achieve ultimate protein products which are not unreasonably expensive. The ultimate aim of in vitro animal cell culture processes is to provide the cells with an environment which closely mimics that which the cells are exposed to in vivo, in terms, e.g., of nutritional requirements, oxygen requirements, temperature, pH, carrying away of wastes, etc., thereby permitting the cells to grow, behave and produce product as they would in vivo, with the added burden of attempting to mimic this environment in larger scale than the microenvironment which normally would be present, for these cells, in the animal itself. At least in theory, it is possible to devise elaborate in vitro systems involving simulations of capillaries, lungs, kidneys and the like to provide the requisite environment, but often not in any remotely cost-effective manner.

A great many in vitro animal cell culture devices and systems are known in the art for culture of both anchorage-dependent cells and cells which can be grown without need for attachment to a substrate. For the culture of animal cells on a sufficiently large scale so as to be potentially suitable for mass production of proteins, among the more popular choices of culture devices is a fermenter in which cells are cultured in suspension in an appropriate culture medium. Anchorage-dependent cells also can be cultured in this way by affixing them to suitable substrate surfaces in the nature of microcarrier particles. Fermenters can be operated on a batch, semi-batch or continuous (perfusion) basis, with periodic or continuous removal of medium from the vessel and replacement with fresh culture medium.

Among the most important "nutrients" for animal cells is oxygen, and the provision of means for supplying the required degree of oxygen to the culturing cells in a suspension culture device poses great difficulties which severely restrict the ability to conduct suspension culture processes at the large-scale (i.e., to support growth of a large number of cells) required to produce ultimate protein products economically.

One means for supplying oxygen to cells in suspension culture is by means of surface aeration, i.e., providing oxygen or oxygen-containing gas in the headspace, above the culture medium level, in the closed culture system. Generally, however, the rate at which oxygen can diffusively transfer from the gas phase to the liquid phase in such systems is relatively low and, thus, growth and maintenance of only a relatively small number of cells can be supported in this manner, relegating it to utility only in small suspension culture vessels. The rate of gas transfer can be increased if the liquid phase is agitated (e.g., as in a stirred reactor), but the increase in gas transfer achievable in this manner is not so great as to offer utility in anything other than relatively small systems.

Another means for providing oxygen to cells in suspension culture is to bubble gas directly through the culture (direct sparging). Apart from providing oxygen to the cells, direct sparging can also be relied upon to bring about circulation of the suspension in the vessel, e.g., based upon fluidizing principles or draft tube devices and the like. While direct sparging is a very efficient means of oxygenation, it generally is very damaging to animal cells. Also, sparging leads to foam formation which itself can damage the cells. Although the use of surfactants can eliminate foam formation, the presence of the surfactant in the eventually harvested culture medium can lead to very difficult and expensive problems in purification of the desired secreted protein product.

It also has been proposed to provide oxygen to cells in suspension culture medium by indirect sparging, i.e., passing oxygen into or on one side of a gas-permeable (but generally liquid-impermeable) tube or membrane arranged in the medium (e.g., silicone rubber tubes or sheets), and through or across which the oxygen permeates into the culture medium. It is generally possible in this way to achieve bubble-free and foam-free aeration, but such methods generally do not provide sufficient gassing efficiency to support the growth of a large number of cells in stirred reactors, due to a combination of moderate gas transfer coefficients (less than about 0.1 cm/min in stirred reactors) and a low ratio of membrane surface to liquid volume imposed by the size and design of stirred reactors.

Another means for providing oxygen to cells in suspension culture is by sparging oxygen into the interior of a wire mesh cylinder suspended in the medium from a top cover plate over the fermentation vessel. The mesh surfaces, which are permeable to gases and liquid, tend to reduce bubbles as the gas sparged on the gas side of the mesh enters and dissolves in the liquid phase on the liquid side of the mesh, and in this way minimize damage to cells. The difficulty with such arrangements, however, is that the ability of the oxygen to efficiently transfer into the liquid phase across the screen or mesh is dependent upon the relative velocity of liquid (culture medium) in contact with the mesh on the liquid side. Thus, in order to achieve sufficient gas transfer to oxygenate the medium to the degree needed to support a large number of cells, the wire mesh cylinder must be rotated or vibrated (thereby increasing the relative velocity between the mesh surface and the liquid phase thereat). This in turn requires resort to rotating mechanical seals and/or other like moving parts which are well-known to serve as potential areas for contamination of the desired sterile environment within the fermenter.

SUMMARY OF THE INVENTION

It is a primary object of the present invention to provide a means for supplying oxygen to an in vitro suspension culture of animal cells in a fermenter or other like vessel.

Another object of the invention is to provide an apparatus for supplying oxygen to a suspension culture of animal cells as described, in a manner which efficiently delivers oxygen at a rate and in an amount capable of supporting the growth of a large number of animal cells.

Yet another object of the invention is to provide an apparatus for supplying oxygen to a suspension culture of animal cells as described, which substantially minimizes bubble and foam formation and damage to the cells.

Still a further object of the invention is to provide an apparatus for supplying oxygen to a suspension culture of animal cells as described, which does not involve or require movement of the apparatus, the use of mechanical seals or the like.

These and other objects as will be apparent are achieved in the present invention by provision of a static oxygenation apparatus adapted to rest or be otherwise arranged in a suspension culture vessel, and adapted to have portions thereof immersed in the liquid culture medium in the vessel and portions thereof residing above the level of culture medium in the vessel.

The oxygenation apparatus is comprised of a bottom section or portion comprised of generally concentric outer and inner hollow cylinders (i.e., cylindrical shells) whose surfaces are made up of porous, gas-permeable, liquid-permeable material of specified average pore size, such that an annular cylindrical space exists between the outer surface of the inner cylinder and the inner surface of the outer cylinder. The apparatus continues with an upper section or portion which is comprised of vertical extensions of both the inner and outer cylindrical shells but whose circumferential surface continuity is interrupted so as to form one or more liquid overflow or weir areas at the base area where the vertical extensions begin. Because they involve extensions of the concentric cylindrical shells, the vertical extensions (which are essentially arcuate sections of the concentric cylinders) also include a continuation of the annular space between the cylinder surfaces. In the preferred embodiment, at least two such weir areas are provided, and as a consequence the vertical extensions of the inner and outer cylindrical shells are non-contiguous and define weir areas at the base area between the non-contiguous vertical extensions.

The apparatus is designed so as to be adapted to communicate with, or preferably be integral with, an annular gas sparging ring at the base of the concentric cylinders which directs oxygen-containing gas into the annular space between the concentric cylinders.

Preferably, the apparatus will further comprise a perforate top closure or closures for the vertical side wall continuations, and one or more vertically-oriented baffles affixed to selected outer areas of the outer cylindrical side wall.

In operation, the oxygenation apparatus is generally centrally arranged in the suspension culture vessel e.g., by suspending it from a top cover plate over the vessel by means of suitable supports) so that the open inner area of the apparatus (i.e., the open area radially inward of the inner concentric cylinder and the open inner area of the annular gas sparging ring associated with the oxygenator) lies generally directly above an impeller operating near the bottom of the culture vessel which is operated in a manner to achieve a bulk axial flow of the culture medium/cell suspension within the culture vessel. Taking into account the liquid displacement caused by the apparatus, the apparatus is arranged in the vessel such that the overflow areas of the apparatus generally are just below the operating liquid (culture medium) level in the vessel (and, thus, the vertical extensions of the side wall cylinders lie generally above the level of the liquid). Oxygen or oxygen-containing gas is sparged through appropriately-sized holes in the gas sparging ring base and then proceeds upward in the annular space between the concentric side wall mesh cylinders. Culture medium flowing up into the inner open area of the apparatus as well as down, around, and through the porous surfaces and the apparatus, is oxygenated by gas within and passing through the porous surfaces.

In accordance with the invention, gas sparged into the annular area between the porous concentric shells of the bottom portion of the apparatus and dissolved in the medium therein delivers oxygen essentially bubble-free across the porous surfaces to culture medium in contact with or proximate to those surfaces. The oxygen transfer rate to the medium is attained at values high enough to support the growth of high cell densities by virtue of the high rate of gas flow into the annular space, the bubble-free transfer across the porous surfaces, the relatively large area over which gas transfer occurs, and the attainment of high relative velocity between the stationary porous surfaces and the medium by appropriate selection of vessel impeller type and speed and by baffling associated with the vessel walls and/or the oxygenator surfaces. As a consequence, it is not necessary to effect movement (vibration/rotation) of the oxygenator and, hence, troublesome mechanical seals are avoided.

An important feature of the invention is that foam formation which would otherwise be brought about by virtue of the excess gas necessarily exiting from the upper end of the annular space is avoided by arranging that this gas escape into the headspace of the vessel rather than into the liquid. Thus, by virtue of the overflow weirs in the apparatus, the liquid level will be maintainable at a fairly constant level, and the vertical extensions of the concentric mesh cylinders, lying above the liquid level, serve as areas for exit of all sparged gas not transferred across porous surfaces to the culture medium in the lower portion of the oxygenation apparatus. The porous surfaces through which the gas escapes into the headspace serve to break up foam which has formed in the culture medium in the annular space, and, as described hereinafter, yet additional means can be employed to break or suppress foam in this area.

Further description of the invention is provided hereinafter with reference to the drawings.

BRIEF DESCRIPTION OF THE DRAWINGS

FIG. 2 represents a perspective view of the gas sparging ring base preferably utilized with the oxygenation apparatus according to the invention, along with support ribs for construction of the oxygenation apparatus in the preferred embodiment of the invention.

FIG. 3 represents a sectional view of the interior of a suspension culture vessel in which the oxygenation apparatus according to the invention is employed.

DETAILED DESCRIPTION OF THE INVENTION

Figure 1:
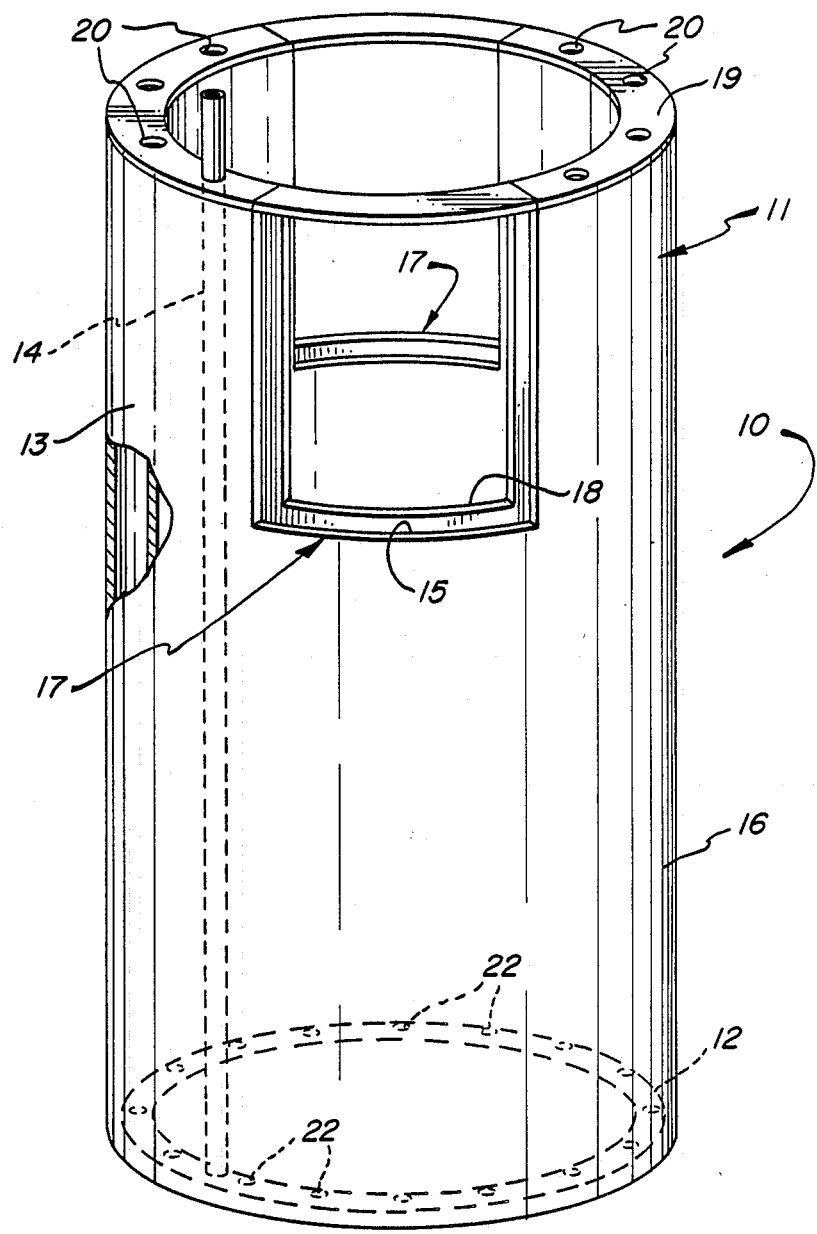
FIG. 1 represents a perspective view of the static oxygenation apparatus according to the invention.

With reference to FIG. 1, the oxygenation apparatus of the invention (generally designated as 10) comprises an annular gas sparging ring base 12 connected to a tube 14 through which gas is delivered to the sparging ring from a source outside the culture vessel (i.e., an extension of tube 14 through a cover plate over the vessel). The sparging ring 12 generally will be a donut-like tube or pipe (e.g., of stainless steel) having an entry port for gas from tube 14 and a plurality of sparging holes or nozzles 22 through which gas is sparged.

Emanating from the general area of the outer periphery of the sparging ring 12 is an upstanding outer cylinder 16 of, e.g., gas-permeable and liquid-permeable wire mesh material, and emanating from the general area of the inner periphery of the sparging ring 12 is an upstanding inner cylinder 18 also of, e.g., wire mesh material. As a consequence of the spacing of the concentric cylinders 16 and 18, an annular space 15 exists of the same general dimension as that of the annular gas sparging ring 12.

At a predetermined point along the vertical length of concentric cylinders 16 and 18, which point is determined based upon the operating culture medium level in the suspension culture vessel in which the oxygenation apparatus is employed, the circumferential surface continuity of the concentric cylinders 16 and 18 is interrupted so as to provide one or more overflow or weir areas such as seen at 17. The unit then continues with vertical extensions of the concentric cylinders and their annular spacing (designated as 11 and 13) to a final predetermined height, such extensions being non-contiguous where, as here, two or more weir areas are provided. In the preferred form of the invention, the apparatus further includes an annular closure cover 19, which can be provided with a plurality of holes 20 in communication with the annular area between the concentric cylinders in their vertical non-contiguous extensions 11 and 13. Although shown as a continuous annular closure, closure cover 19 may alternatively consist of discrete separate covers only for the vertical non-contiguous extensions 11 and 13.

For constructing the oxygenation apparatus shown in FIG. 1, a number of alternative procedures are available. If the material of the cylinders possesses sufficient dimensional and structural stability, the cylinders can be pre-constructed to desired height and in desired diameter and then affixed at their base to the outer and inner peripheries of the annular sparging ring 12. As will more typically be the case, however, the material forming the cylinders will be somewhat flexible (e.g., fine wire mesh) and pre-construction of cylinders therefrom may be problematic. In such cases, it is preferred to utilize the annular sparging ring 12 as the base for a skeletal structure (see FIG. 2) which can be used to support and give dimensional stability to the cylinders. Thus, annular sparging ring 12 can be pre-constructed with a number of upstanding ribs 24 disposed at predetermined areas about its circumference. The ribs can be any suitable solid or hollow pipes, rods, tubes, or the like, and indeed one such rib may consist of gas entry tube 14. The material (e.g., wire mesh) of the cylinders can then be formed along the inner areas of the ribs to form the inner concentric cylinder 18 and also formed along the outer areas of the ribs to form the outer concentric cylinder 16, with the annular spacing between the cylinders being generally established by the thickness of the ribs 24. Generally, the concentric cylinders 16 and 18 will be formed to the full height of the oxygenation apparatus and then cut back from the top to form one or more weir areas 17 and the vertical extensions of the concentric cylinders (e.g., 11 and 13). As such, ribs 24 can be constructed all of the same length (in which case the weir areas 17 would be formed in areas between ribs) or can be constructed such that some will extend to the full height of the unit and others (e.g., where weir areas 17 will exist) made appropriately shorter. Some or all of ribs 24 also may be extended in length to serve as support rods for suspending the oxygenation unit from a top cover plate of the suspension culture vessel.

FIG. 3 shows the arrangement of oxygenation apparatus 10 within a suspension culture vessel generally designated as 100. In this view, the oxygenation apparatus 10 is suspended from the cover plate 104 over the culture vessel by means of extensions of two or more of the ribs 24 used to construct the oxygenator. Taking into account the liquid displacement caused by the introduction of the oxygenation unit, the unit is suspended such that the operating liquid level 102 in the vessel resides just above weirs 17. Annular gas sparging ring 12 is supplied with gas from gas tube 14 which extends through cover plate 104 and is there connected to a source of oxygen or oxygen-containing gas (not shown). The oxygenation unit also is shown with baffles 40 affixed thereto for helping to promote axial liquid flow past the oxygenator gassing surfaces as imparted by impeller 106. Baffles also can be arranged in association with the interior walls of the suspension culture vessel 100 and/or suspended from a cover plate over the vessel. The suspension culture vessel 100 also is provided with culture medium inlet port 108, culture medium outlet port 110, and gas outlet port 112.

In operation, culture medium and cells suspended therein (either alone or affixed to microcarriers) are circulated throughout the vessel 100 under influence of the impeller 106 and baffles 40. The impeller 106 is operated such that the liquid culture medium will be encouraged to flow upward through the hollow interior of the inner concentric cylinder of the oxygenation apparatus and/or upward past the outer surface of the outer concentric cylinder (as well obviously into and through the annular area between the concentric cylinders since the mesh material thereof is liquid permeable) whereupon it reaches the overflow weir areas 17 and then passes down around the external and/or internal areas of the oxygenation unit as the case may be. Gas passed from gas tube 14 into annular sparging ring 12 progresses up through the annular space 15 between the concentric cylinders and delivers gas, generally bubble-free, through the mesh surfaces to culture medium flowing in contact with or near such surfaces. As gas continues up in the annular space 15 beyond the liquid level (i.e., in the inner space between the cylinder sections in the vertical extensions above the weirs), it exits through the mesh areas into the headspace area above the liquid, where it can continuously or periodically be released through gas exit line 112. Although gas bubbles and foam will exist in the culture medium in the annular space into which gas is sparged, the porous mesh surfaces not only permit the gas therein to transfer essentially bubble-free across these surfaces into the medium outside the annular space, but also serve to break up foam as gas is released, through the porous mesh surfaces of the vertical extensions, into the vessel headspace area. In the embodiment shown, closure cover 19, having holes 20 in communication with the space between the concentric cylinder extensions and the annular space between the concentric cylinders therebelow, can be employed to break foam which may have formed in these annular areas. Thus, fresh culture medium fed to the culture vessel 100 by inlet port 108 can be arranged to feed through holes 20 in the nature of a gentle spray which is capable of breaking foam present in the medium present in annular spaces.

The material of the concentric cylinders 16 and 18 and their vertical extensions (e.g., non-contiguous extensions 11 and 13), although described above as wire mesh, can be an gas-permeable, liquid-permeable porous material, preferably a stainless steel filter cloth. The porous apertures in the material generally are sized in a compromise of several competing factors. Generally speaking, it is desirable to prevent cells from entering the interior of the oxygenator in an effort to minimize cell damage by reason of the high energy oxygenation occurring in such area. However, sizing the apertures so small as to preclude passage of cells therethrough greatly reduces the mass transfer of oxygen into the liquid phase and also disadvantageously enhances the possibilities of aperture-clogging and fouling by cells and cell colonies. Accordingly, the apertures in the porous material of the cylinders generally will be chosen to be in the range of from about 10 to 150 microns, preferably from about 30 to 100 microns. If desired, the materials used for the inner and outer concentric cylinders can be different and of different pore size, and (although making the construction substantially more difficult) the materials used and/or the pore size in the vertical degassing extensions (i.e., above the weir areas) can be different from those used to construct the gassing cylinders in contact with the medium.

As will be appreciated, the oxygenation apparatus of the present invention consists in its essential elements of a bottom portion comprised of concentric cylinders of gas-permeable, liquid-permeable porous material and a top portion comprised of vertical extensions of such concentric cylinders whose circumferential surfaces have been interrupted such that one or more overflow weirs are formed. For ease of construction, the sparging ring will be made part and parcel of the oxygenation apparatus, and preferably easily removable therefrom so as to facilitate cleaning of the inside of the oxygenator, but it is also possible to have the sparging ring separate from the oxygenator but designed and arranged in a culture vessel so as to direct gas up through the annular area between the concentric cylinders.

Also, while the oxygenation apparatus has been shown in use as suspended from the top of the suspension culture vessel, it should be apparent that the unit also could be adapted to rest within the vessel, as by use of legs or stand-offs which permit the oxygenator to be supported by the vessel bottom walls yet occupy a position above the impeller.

All materials used in construction of the oxygenation apparatus according to the invention obviously will be chosen so as to be compatible with cell culturing and to be susceptible of sterilization. Particularly preferred are materials such as stainless steel.

An important advantage of the present invention is the ability of the oxygenator to deliver a required large quantity of oxygen to circulating liquid culture medium without need for rotation or vibration of the oxygenator as a means for increasing the relative liquid velocity past its surfaces and thereby increase gas transfer. As such, mechanical seals and the like are unnecessary, greatly reducing the risk of violating the sterile culture environment. In addition, because of the ease of construction and the operating principles involved, the oxygenator can be readily and predictably scaled for use in larger or smaller culture vessels than that for which an original construction has been optimized.

The overall size of the oxygenation apparatus and specific dimensions of portions or areas thereof are not per se critical, but simply are chosen to provide sufficient surface area for the bottom portion (at which transfer of oxygen to the medium occurs) and sufficient surface area of the top portion (i.e., the vertical extensions through which gas transfers to the vessel headspace), as well as a sufficient annular space into which to sparge gas, and sufficient weir area (through one or more weirs) to achieve the desired overflow of medium thereat and maintenance of liquid operating level. Generally speaking, it is preferred that the weir area occupy at least about 25% of the cylinder perimeters, and more preferably at least about 50% of the perimeters. Thus, in the figures, two weir areas are provided, each representing an arc section of the cylinders of about 90°, thereby giving a weir area occupying about 50% of the total circumference of the cylinders. Because the weir areas represent subtractions from the otherwise cylindrical surfaces in the upper portion of the oxygenator where degassing into the headspace occurs, the size of the weir areas will also have an effect on the available degassing area, which can be increased of course by increase in the height of the vertical extensions. Generally speaking, anywhere from about 50 to 80% of the overall height of the oxygenator will be devoted to oxygenation of the culture medium (i.e., will be below the weir level) with the remainder of the height devoted to the degassing area above the weir level.

For a typical application, for use in a stirred suspension culture reactor having a working volume of about 36 liters, the oxygenator apparatus can be composed of concentric cylinders having respective diameters of about 17.5 and 20.0 cm, and an overall height of about 67 cm, with two non-contiguous weir areas beginning at 50 cm from the bottom, each occupying a 90° arc section of the cylinders. In such an arrangement, at a typical vessel impeller speed of 100 rpm (7 cm ⌀ pitch blade impeller), and for attaining a 50% air saturation of the culture medium (5% serum in basal medium), oxygen transfer rates (utilizing air as the source of oxygen) of between about 0.0065 $\mu M$ $O_2$/ml/min and 0.0136 $\mu M$ $O_2$/ml/min are obtained for gas flow rates of from 0.50 up to 1.0 liters $O_2$/min, and still further up to about 0.1 $\mu M$ $O_2$/ml/min utilizing pure oxygen at a gas flow rate of 1.6 volumes gas/volume reactor/hour (based on a mass transfer coefficient of up to 0.7 cm/min under these conditions; this is more than five times the transfer efficiency of silicone tubing oxygenators reported in the literature). At the latter oxygen transfer rate, for an oxygen consumption rate of typical hybridoma cells in suspension of about $1.33 \times 10^{-3}$ $\mu M$ $O_2/10^6$ cells/min, the culture medium oxygenated with the earlier-described apparatus is capable of supporting the growth of $7.7 \times 10^7$ cells/ml.

It should be understood, of course, that the apparatus of the present invention, while described as an oxygenator, can also be employed to deliver other or additional gases to a culture medium simply by appropriate variation of the gas stream fed to the sparging device. In particular, carbon dioxide may be included in the oxygen-containing gas and/or fed alone to the sparging device as a means for adjusting the pH of the culture medium as is well known in the art. In addition, the apparatus obviously may be employed to provide oxygen or other gases to liquids other than culture medium.

Although the invention has been described with reference to particular embodiments and typical constructions, dimensions, capabilities and the like, these are intended as illustrative of, rather than limitations on, the scope of the invention as defined by the appended claims.

What is claimed is:

1. A static apparatus for oxygenating a suspension culture of animal cells in a liquid culture medium, comprising a bottom portion comprising generally concentric vertically-oriented inner and outer hollow cylinders, the walls of which are composed of porous gas-permeable, liquid-permeable material, so as to provide between the cylindrical surfaces of said concentric cylinders a hollow annular space adapted to receive oxygen-containing gas and transfer at least a portion of said gas substantially bubble-free across said porous material to a liquid phase in contact with or in proximity to said cylindrical surfaces of said bottom portion; and a top portion comprising vertical extensions of said concentric cylinders which are interrupted at least one area along their circumferential surfaces such that at least one liquid overflow area is defined at the base area at said interrupted surfaces, and such that a continuation of sections of said hollow annular space exists between the vertically-extended surfaces of said concentric cylinders, said continuation of said sections of said hollow annular space being adapted to receive oxygen-containing gas from said hollow annular space of said bottom portion and to release oxygen-containing gas across said porous material above said overflow areas, said apparatus being adapted to be stationarily arranged in a suspension culture vessel and unassociated with means for rotating or vibrating said apparatus.

2. The apparatus according to claim 1 further comprising means for adapting said oxygenating apparatus to be suspended into the interior of a suspension culture vessel from a top closure surface of said suspension culture vessel.

3. The apparatus according to claim 1 wherein said porous gas-permeable, liquid-permeable material is wire mesh.

4. The apparatus according to claim 1 wherein said porous gaspermeable, liquid-permeable material is stainless steel filter cloth having apertures in the range of from about 10 to 150 microns.

5. The apparatus according to claim 1 further comprising vertically oriented baffle means emanating from the outer surface of said outer hollow cylinder.

6. The apparatus according to claim, further comprising annular sparging means, arranged within said hollow annular space at the base of said concentric cylinders in said bottom portion, for sparging oxygen-containing gas upwardly into said hollow annular space and said continuation of sections of said hollow annular space.

7. The apparatus according to claim 6 further comprising means, in gaseous communication with said annular sparging means, for delivering oxygen-containing gas to said annular sparging means.

8. The apparatus according to claim 7 further comprising vertical support means, emanating from said annular sparging means, for supporting the surfaces of said concentric cylinders and said vertical extensions thereof.

9. The apparatus according to claim 1 further comprising planar closure means for covering said sections of said hollow annular space at the upper terminal portion of said vertical extensions of said concentric cylinders.

10. The apparatus according to claim 9 wherein said closure means contain a plurality of through-holes in communication with said sections of said hollow annular space therebelow.

11. A static apparatus for oxygenating a suspension culture of animal cells in a liquid culture medium, comprising a bottom portion comprising an annular gas sparging ring base; an outer cylindrical wall, composed of porous gas-permeable, liquid-permeable material, upstanding from the outer periphery of said annular base to a predetermined vertical height; and an inner cylindrical wall, composed of porous gas-permeable, liquid-permeable material, substantially concentric with said outer cylindrical wall, upstanding from the inner periphery of said annular base to about the same predetermined height of said outer cylindrical wall, such that an annular cylindrical space exists between the surfaces of said substantially concentric cylindrical walls; a top portion comprising non-contiguous vertical extensions of said inner and outer cylindrical walls such that within said extensions there exists a continuation of sections of said hollow annular space; and means for providing oxygen-containing gas to said annular gas sparging base, said apparatus being adapted to be stationarily arranged in a suspension culture vessel and unassociated with means for rotating or vibrating said apparatus.

12. A static apparatus for oxygenating a liquid, comprising a bottom portion comprising generally concentric vertically-oriented inner and outer hollow cylinders, the walls of which are composed of porous gas-permeable, liquid-permeable material, so as to provide between the cylindrical surfaces of said concentric cylinders a hollow annular space adapted to receive oxygen-containing gas and transfer at least a portion of said gas substantially bubble-free across said porous material to a liquid phase in contact with or in proximity to said cylindrical surface; and a top portion comprising non-contiguous vertical extensions of said generally concentric cylinders such that liquid overflow areas are defined at the base areas between said non-contiguous vertical extensions, and such that a continuation of sections of said hollow annular space exists between the vertically-extended surfaces of said concentric cylinders, and continuation of sections of said hollow annular space being adapted to receive oxygen-containing gas from said hollow annular space of said bottom portion and to release oxygen-containing gas across said porous material, above said overflow areas, said apparatus being adapted to be stationarily arranged in a suspension culture vessel and unassociated with means for rotating or vibrating said apparatus.

* * * * *

UNITED STATES PATENT AND TRADEMARK OFFICE
CERTIFICATE OF CORRECTION

PATENT NO. : 4,960,706
DATED : Oct. 2, 1990
INVENTOR(S) : Rudolf F. Bliem, James F. Long It is certified that error appears in the above-identified patent and that said Letters Patent is hereby corrected as shown below:

Column 1, line 22, change "o" to -- to --

Column 9, (Claim 1, 14th line in claim), before "least" insert -- at --

Column 9, (Claim 6, 1st line in claim), after "claim" insert -- 1 --

Column 10, (Claim 12, 11th line in claim), change "surface"
      to -- surfaces --

Column 10, (Claim 12, 18th line in claim), change "and" to -- said --

Signed and Sealed this

Twenty-fourth Day of December, 1991

Attest:

HARRY F. MANBECK, JR.

*Attesting Officer*　　　　　*Commissioner of Patents and Trademarks*